United States Patent [19]

Minami

[11] Patent Number: 4,647,378
[45] Date of Patent: Mar. 3, 1987

[54] BLOOD DIALYZING METHOD AND APPARATUS

[75] Inventor: Hiromichi Minami, Takarazuka, Japan

[73] Assignee: Nihon Medical Engineering Co., Ltd., Hyogo, Japan

[21] Appl. No.: 596,264

[22] Filed: Apr. 3, 1984

[30] Foreign Application Priority Data

Mar. 31, 1983 [JP] Japan ................. 58-57147
Mar. 31, 1983 [JP] Japan ................. 58-57148
Mar. 31, 1983 [JP] Japan ............. 58-48614[U]

[51] Int. Cl.[4] ............................................. B01D 13/00
[52] U.S. Cl. ........................................ 210/646; 210/90; 210/321.3
[58] Field of Search ................. 210/646, 321.3, 90

[56] References Cited

U.S. PATENT DOCUMENTS 3,946,731  3/1976  Lichtenstein ............. 210/87 X
4,252,651  2/1981  Soperstrom ............. 210/929 X
4,370,983  2/1983  Lichtenstein ............ 210/929 X

FOREIGN PATENT DOCUMENTS 0004284  1/1979  Japan ....................... 210/929

Primary Examiner—Frank Spear
Attorney, Agent, or Firm—Koda and Androlia

[57] ABSTRACT

A blood dialyzing apparatus having a dialyzer with blood and dialysate chambers defined therein comprises a blood pump for pumping the blood from a cannula, pierced in the patient's A-V fistula, back to the patient's A-V fistula through the blood chamber of the dialyzer, and a fluid circuit for the supply of a dialyzing solution past the dialysate chamber. The fluid circuit includes first and second shut-off valves disposed adjacent the inlet and outlet of the dialysate chamber, respectively, while a pressure sensor is provided to detect the pressure of the blood flowing upstream of the blood pump and also upstream of the blood chamber. When the pressure of the blood so detected attains a value equal to or lower than a predetermined value, the first and second shut-off valves are closed on the one hand and the ultrafiltration pressure in the dialyzer becomes substantially zero.

8 Claims, 7 Drawing Figures

BLOOD DIALYZING METHOD AND APPARATUS

BACKGROUND OF THE INVENTION

The present invention generally relates to the blood dialysis and, more particularly, to a method for blood dialysis and an apparatus for the removal of waste products of metabolism from the blood by the use of a dialyzer. The method and apparatus herein disclosed according to the present invention are effectively utilized for the automation of the blood dialysis at a minimized energy-consumption.

A technique of blood dialysis by the use of a dialyzer, or an artificial kidney as it is generally known, has long been widely practiced to purify the human blood by the removal of waste products of metabolism in the body of a patient with the dialyzer functioning in lieu of a kidney in the case of the kidney failure.

Since the method and apparatus to which the present invention pertains is concerned with the utilization of a positive ultrafiltration pressure in the dialyzer for the diffusion of waste products of metabolism from the blood into the dialyzing solution, the prior art system wherein the positive ultrafiltration pressure is similarly utilized will now be discussed in detail with particular reference to FIG. 1 of the accompanying drawings.

Figure 1:
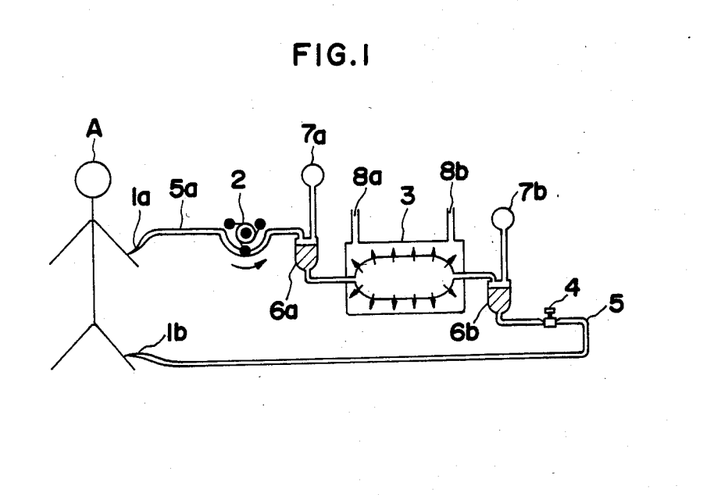
FIG. 1 is a schematic diagram showing the prior art dialyzing apparatus including the dialyzer unit and its extracorporeal blood circuit, reference to which has already been made in connection with the discussion of the prior art.

FIG. 1 illustrates schematically an extra-corporeal blood circuit extending from an artery to a vein, for example, from a radial artery to a saphenous vein of a patient A, in which circuit the prior art dialyzing apparatus is placed. The extracorporeal blood circuit shown therein includes an inlet cannula 1a, inserted into the radial artery, and an outlet cannula 1b inserted into the saphenous vein. According to the prior art, the blood to be dialyzed and flowing into the inlet cannula 1a is pumped by a blood pump 2 so as to flow towards a dialyzer unit 3 through a tubing 5a and then towards the outlet cannula 1b through a tubing 5 after having passed through a blood chamber in the dialyzer unit 3. The blood so flowing to the outlet cannula 1b after the waste products of metabolism have been removed therefrom is eventually returned to the saphenous vein of the patient A. In addition to the blood chamber, the dialyzer unit 3 has a dialysate chamber communicating through a solution inlet 8a to a source of dialyzing solution on the hand and through a dialysate outlet 8b to any suitable dialysate disposing container on the other hand. In order to achieve the positive ultra-filtration, that is, in order to create a pressure difference between the flow of the blood within the blood chamber and that of the dialyzing solution within the dialysate chamber to enable the waste products of metabolism contained in the blood to be forced into the dialysing solution through a membrane within the dialyzer unit 3, the tubing 5 on the downstream side with respect to the direction of flow of the blood towards the outlet cannula 1b has a flow regulator 4 for adjustably constricting the tubing 5. For monitoring the ultrafiltration pressure, a portion of the tubing 5a between the pump 2 and the dialyzer unit 3 and a portion of the tubing 5 between the dialyzer unit 3 and the flow regulator 4 have respective air traps 6a and 6b disposed thereon and fluid-coupled to associated pressure gauges 7a and 7b.

When in use for the blood dialysis, the blood pump 2 is operated to effect the extracorporeal circulation of the blood through the extracorporeal blood circuit by way of the dialyzer unit 5 while the flow regulator 4 is adjusted in the light of readings of the pressure gauges 7a and 7b to create a proper positive ultrafiltration pressure.

As is well known to those skilled in the art, a primary function of the kidney is to form urine, the main constituent of which is a water component. Accordingly, when it comes to the blood dialysis, the removal from the blood of an excessive water component containing the waste products of metabolism is one of the major concerns that cannot be neglected. In other words, while the water component within the body is transferred into the blood having flowed within the cells and then into the blood vessels through the interstices among the cells, the removal of the excessive water component containing the waste products of metabolism has to be done at a rate conforming to the rate of transfer of the water component into the blood. However, not only because the rate of transfer of the water component into the blood differ from patient to patient, but also because for a patient it changes with time each day, it is not easy to grasp it without difficulty. In addition, the water removal is affected by numerous factors such as, for example, the ultrafiltration pressure, the type and the total surface area of the semipermeable membrane or membranes used in the dialyzer unit, the time during which the dialysis is carried out, the rate of flow of the blood and the difference in osmotic pressure between the dialyzing solution and the blood.

Of these factors, the type and the total surface area of the semipermeable membrane or membranes are determined by the type of dialyzer unit employed, and accordingly, by suitably selecting a particular type of dialyzer unit to be employed, the problem associated therewith can be solved. The difference is osmotic pressure between the dialyzing solution and the blood has been found not affect the water removal appreciatively. With respect to the dialyzing interval, that is, the time during which the dialysis is carried out, the longer, the greater the amount of water removed. However, the shorter, the better, because if it extends for a long time, not only is the patient required to be bound to the dialyzing facility, but also care must be taken to water the patient for such a long time.

In view of the foregoing, it can be deduced that in practice the blood dialysis has to be carried out at a controlled blood flow and under a controlled ultrafiltration pressure and both are required to facilitate the removal of the water component so that the required amount of the water component can be removed in a given time interval. For this purpose, the major factor is the stabilized flow of blood through the extracorporeal blood circuit from the patient back to the same patient. However, the blood flow through the extracorporeal blood circuit is limited depending on the physical conditions of a particular patient. In addition, it is extremely difficult for the stabilized flow of blood through the extracorporeal blood circuit to be maintained for a substantially prolonged time partly because a drop in blood pressure would occur as a result of insufficient blood circulation within the patient's body which will occur as a result of the accelerated water removal and partly because of any possible malfunctioning of A-V fistula equipment necessary to draw the blood exteriorly of the patient's body. In particular, the patient suffering from hypotonia as a result of the accelerated water removal during the blood dialysis tends not only to feel discomfort causing, for example, a symptom of vomiting, but also to have a bodily convulsion which, unless care is taken of the patient, will last for a substantial time interval and will, in the worst case, result in death from shock. Accordingly, the utmost care is required once the symptom of hypotonia has been observed in the patient being dialyzed.

On the other hand, if the rate of water removal is lowered for fear of the hypotonia, that is, the drop in blood pressure, during the blood dialysis, no sufficient and satisfactory water removal will be performed with some of the waste products of metabolism consequently left unremoved, imposing an undesirable burden on the blood circulatory system.

Hitherto, regulator blood pressure measurement, that it, a regular sphygnomanometric measurement, is frequently carried out as a precaution against any possible drop in blood pressure which would result from the accelerated water removal. By way of example, in the case of a chronic patient whose kidney failure is substantially stabilized and is, therefore, familiar to the attendant doctor, the blood pressure measurement is carried out at intervals of 15 and 30 minutes at the time of start of the dializing treatment, of 30 to 60 minutes during the course of the treatment, or of 15 to 30 minutes before the termination of the treatment. On the other hand, in the case of the patient receiving the dialyzing treatment for the first time, in the case of the patient being a child or an aged person whose amount of blood being circulated is relatively small, or in the case of the patient who is suffering from, for example, a diabetic disease accompanied by severe arteriosclerosis and who is, therefore, susceptible to hypotonia or coronary insufficiency, the blood pressure measurement is carried out at a number of times greater than that required for routine blood pressure measurement while the rate of the water component being removed is adjusted according to the result of each measurement.

In any event, a qualified nurse is usually charged, under instructions of a doctor, with the work of blood pressure measurement and, if necessary, the adjustment of the rate of water removal. However, once the patient suffers from hypotonia during the dialyzing treatment, the nurse is caused to be busy not only with the regular nursing procedures, but also with extra nursing procedures including, for example, the performance of a transfusion, the administration of drugs, and application of hot or cold dressing, and sanitary matters. Considering that one qualified nurse is assigned to take care of four or five patients, these works occupy a high percentage of the nursing job and, therefore, the nurse is often forced to work hard.

Thus, according to the prior art, the requirement of manual intervention is too high in performing a plurality of such works required to achieve the blood dialysis under satisfactory and effective conditons with the use of a conventional dialyzing method and apparatus, and therefore, numerous problems have arisen such as the increased possibility of occurrence of errors on the part of the caretaker, the heavy labour imposed on the nurse, and the cost incurred not only by a patient, but also by a hospital.

SUMMARY OF THE INVENTION

The present invention has been developed as a result of rearch which the inventors have done as a prolonged period of time and has for its essential object to provide an improved method and an improved apparatus both for the blood dialysis, which can be practiced with the minimum number of blood pressure measurements required and with no substantial need to perform the adjustment of the rate of water removal and at a minimized energy consumption.

Anther important object of the present invention is to provide an improved method and an improved apparatus which are effective to avoid any possible drop in blood pressure which would result from the excessive removal of the water component, and which are efficient in that the rate of water removal can be increased.

A further object of the present invention is to provide an improved method and an improved apparatus both of the type referred to above, which are effective to substantially eliminate the disadvantages and inconveniences inherent in the prior art method and apparatus of a similar kind.

BRIEF DESCRIPTION OF THE DRAWINGS

There and other objects and features of the present invention will become clear from the following description taken in conjunction with preferred embodiments thereof with reference to the accompanying drawings, in which.

DETAILED DESCRIPTION OF THE EMBODIMENTS

Before the description of the preferred embodiments of the present invention proceeds, it is to be noted that like parts are designated by like reference numerals throughout the accompanying drawings for the sake of brevity.

According to the principle of the present invention, in place of the blood pressure measurement hitherto performed by the manual intervention, a pressure sensor is utilized to detect and monitor the pressure of blood flowing through a portion of the extracorporeal blood circuit upstream of a blood pump. This will be described in detail with particular reference to FIG. 2.

Figure 2:
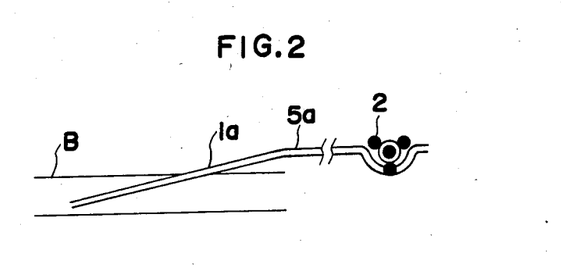
FIG. 2 is a schematic diagram showing a A-V fitsula and a cannula for the purpose of illustration of the principle of the present invention.

Referring first to FIG. 2, a A-V fistula blood flows through a vein B at a A-V fistula pressure b which is usually positive. However, when a cannula $1a$ is stuck into the veil B and the A-V fistula blood is them drawn by a blood pump 2 into a tubing $5a$ through the cannula $1a$, a pressure drop occurs in a quantity c which is substantially inversely proportional to the effective cross sectional area of the cannula $1a$, but is substantially proportional to the flow of blood, that is, the number of revolution of the blood pump 2. Accordingly, the blood pressure within the tubing 5a is equal to the difference between the A-V fitsula pressure b and the quantity c, which difference is usually a negative value and remains constant throughout the dialyzing operation. Although the amount of blood within the blood vessel decreases as the water removal proceeds, a resultant drop in blood pressure is avoided because of the arterial contstriction. However, when the water removal proceeds to such as extent that the artial constriction can no longer prevent the drop in blood pressure, the A-V fistula pressure b decreases to zero or a negative pressure, wherefore the pressure within the tubing 5a, expressed by the difference between the aforementioned pressure b and c, decreases to a value lower than that exhibited during the normal dialyzing operation. Accordingly, it is possible to avoid any possible drop in blood pressure throughout the patient's body if the water removal is interrupted by decreasing the ultrafiltration pressure to a lower value or zero at the time the pressure within the tubing 5a has decreased to a value lower than the predetermined pressure.

Figure 3:
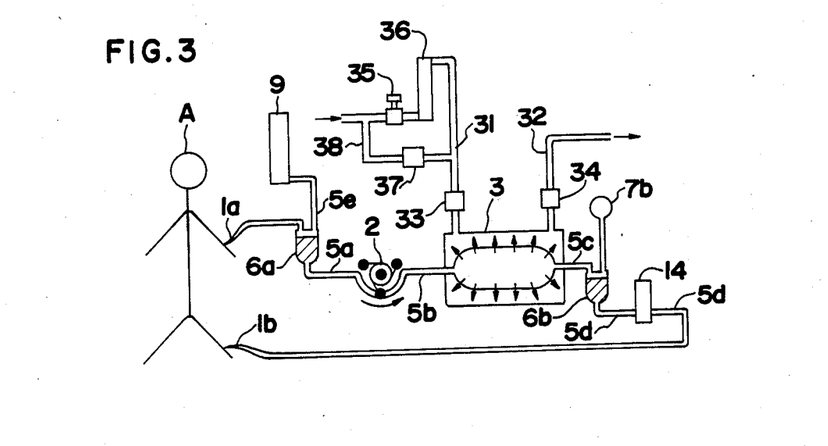
FIG. 3 is a schematic diagram showing a dialyzing apparatus, including a dialyzer unit and its extra-corporeal blood circuit, according to a preferred embodiment of the present invention.
Figure 4:
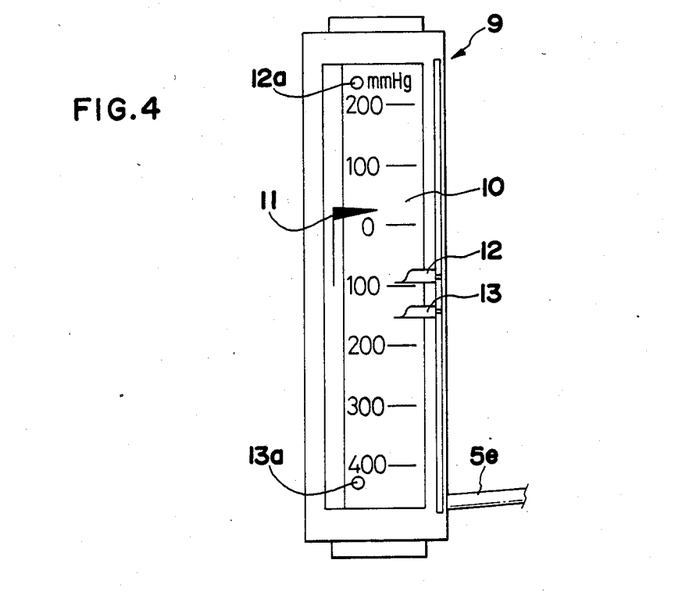
FIG. 4 is a front elevational view of a pressure sensor showing the details of calibrations.

Referring now to FIG. 3 illustrating a preferred form of one embodiment of the present invention in which a positive ultrafiltration pressure is utilized, a portion of the tubing 5a between the cannula 1a and the air pump 2 has an air trap 6a disposed therein and is fluid-connected with a pressure sensor 9 through a pressure sensing tube 5e. As shown in FIG. 4, the pressure sensor 9 has a movable pointer needle 11 movable along a calibrated scale 10 in response to the pressure applied thereto through the pressure sensing tube 5e for the purpose of providing a visual indication of the pressure so detected. For this purpose, the calibrated scale 10 has a series of calibrations ranging from the lowest measurable pressure, for example, −400 mmHg, to the highest measurable pressure, for example, 200 mmHg. The pressure sensor 9 also has first and second manually presettable index needles 12 and 13 and first and second indicator lamps 12a and 13a. The first and second manually presettable index needles 12 and 13 are manually adjustable independently along the calibrated scale 10 to any pressure reading. The pressure sensor 9 of the construction described above is so designed as to generate a first signal R when the pointer needle 11 moved in response to the pressure applied thereto through the tubing 5e aligns with the first index needle 12 and so as to generate a second signal S when the pointer needle 11 aligns with the second index needle 13. The first and second indicator lamps 12a and 13a are lit when the first and second signals R and S are generated, respectively. It is to be noted that, since the tubing 5a and the tube 5e are exposed to the negative pressure, they should be made of a material sufficiently hard to deform under the influence of the negative pressure acting inside these tubings.

The dialyzer unit 3 is of any known construction and has a blood inlet fluid-connected with the blood pump 2 through a tubing 5b and a blood outlet fluid-connected to an air trap 6b and a pressure gauge 7b through a tubing 5c, which is in turn fluid-connected to the cannula 1b through a tubing 5d. A portion of the tubing 5d adjacent to the blood outlet of the dialyzer unit 3, but on one side of the air trap 6b remote from the blood outlet of the dialyzer unit 3 is provided with a positive pressure regulator 14 operable to adjustably clamp the tubing 5d to adjust the effective cross sectional area of the tubing 5d as will be described in detail with reference to FIGS. 5 and 6.

Figure 5:
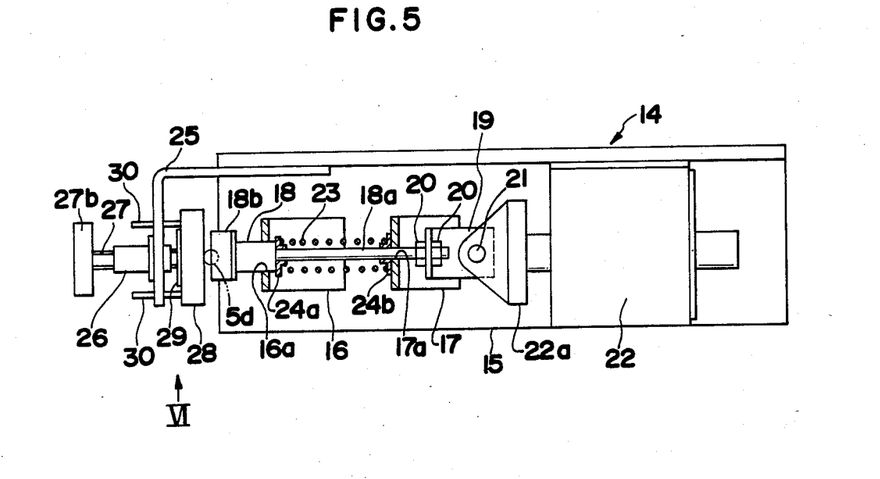
FIG. 5 is a front elevational view, with parts shown in section, of a positive pressure regulator used in the apparatus of FIG. 3.

Referring first to FIG. 5, the positive pressure regulator 14 comprises a generally L-sectioned bench 15 having a pair of spaced guide brackets 16 and 17 rigidly mounted thereon with guide bores 16a and 17a in the respective guide brackets 16 and 17 aligned with each other. A generally elongated slide piece 18 having its right-hand end portion formed into a connecting rod 18a of reduced diameter is axially slidably supported by the brackets 16 and 17 with the slide piece 18 and the rod 18a extending respectively through the guide bores 16a and 17a. The free end of the rod 18a integral with the slide piece 18 is exteriorly threaded and is secured by means of fastening nuts 20 to a connecting piece 19 which is in turn connected through a connecting pin 21 to a plunger 22a of a solenoid unit 22 rigidly mounted on the bench 15. On the other hand, the free end of the slide piece 18 opposite to the rod 18a is formed into, or otherwise provided with, a conical member 18b adapted to compress the tubing 5d to adjust the effective cross sectional area thereof in a manner as will be described in detail later. The rod 18a, has a compression spring 23 mounted therearound and extending between a pair of spaced washers 24a and 24b mounted thereon, and by the action of this compression spring 23, the slide piece 18 is normally biased to the left as viewed in FIG. 5.

Figure 6:
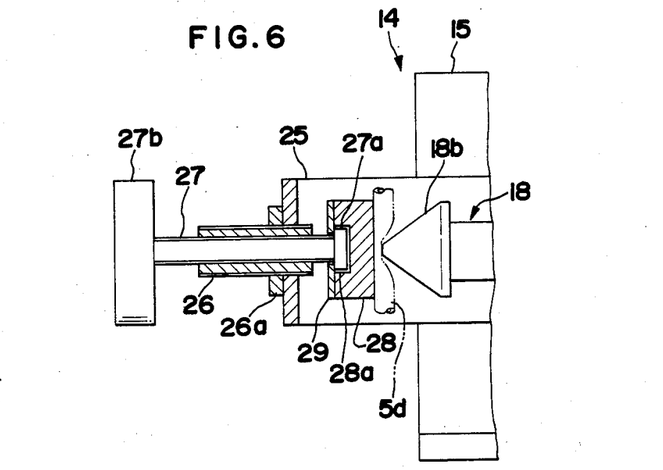
FIG. 6 is a cross-sectional view, on an enlarged scale, of a portion of the positive pressure regulator as viewed in a direction shown by the arrow VI in FIG. 5.

The positive pressure regulator 14 also comprises an adjustment screw 27 axially adjustably supported by a sleeve member 26 which is in turn threadedly supported by a generally L-shaped bracket 25, rigidly secured to the bench 15, so as to align with the slide piece 18. The sleeve member 26 is adapted to be secured in position by means of a lock nut 26a exteriorly threadingly mounted thereon and held in abutment with the bracket 25. The adjustment screw 27 has one end formed with a knob 27b accessible to the hand of an operator and the other end carrying a tailstock 28 for the support of the tubing 5d in a manner which will now be described. As best shown in FIG. 6, the tailstock 28 has a recess 28a defined therein so as to extend inwardly of the tailstock 28 from one surface thereof opposite to the surface of the tailstock 28 to which the tubing 5d is held when the latter is to be clamped to adjust the effective cross sectional area thereof. This tailstock 28 is mounted on the adjustment screw 27 with a head 27a loosely received in the recess 28a, said head 27a being connected to, or otherwise integrally formed with, said other end of the adjustment screw 27. For avoiding any possible separation of the tailstock 28 from the head 27a, a stopper plate 29 having an opening defined therein of a diameter slightly greater than the maximum outer diameter of the screw 27, but smaller than the diameter of the head 27a is secured to the tailstock 28 with the adjustment screw 27 loosely extending therethrough. For avoid arbitrary rotation of the tailstock 28 about the head 27a, a pair of juxtaposed guide rods 30 are connected to the tailstock 28 and are in turn slidably guided through respective bearing holes (not shown) defined in the bracket 25 substantially as shown in FIG. 5.

The positive pressure regulator 14 of the above described construction is so designed that, while the tubing 5d extends between the conical member 18b fixed to the slide piece 18 and the tailstock 28, the effective cross sectional area of the tubing 5d can be adjusted by turning the knob 27b to move the adjustment screw 27 and, hence, the tailstock 28 in a direction towards or away from the conical member 18b. In other words, when the knob 27b is turned to move the adjustment screw 27 in a leftward direction as viewed in FIGS. 5 and 6, that is, in a direction towards the conical member 18a, the effective cross sectional area of the tubing 5d is reduced, whereas whtn the knob 27b is turned to move the adjustment screw 27 in a rightward direction as viewed in FIGS. 5 and 6, that is, in a direction away from the conical member 18a, the effective cross sectional area of the tubing 5d is increased. However, when the solenoid unit 22 is electrically energized while the tailstock 28 has been moved leftwards to reduce the effective cross sectional area of the tubing 5d, the plunger 22a is retracted, that is, moved in a direction towards to the solenoid unit 22, to pull the slide piece 18, connected thereto through the connecting pin 21 and the coupling member 19, in a leftward direction as viewed in FIG. 5 against the compression spring 23, thereby resulting in the separation of the conical member 18b from the tubing 5d to release the clamping force from the tubing 5d. Conversely, the deenergization of the solenoid unit 22 results in the claimping of the tubing 5d to the preset effective cross sectional area determined by the positioning of the adjustment screw 27 and, hence, the tailstock 28. As a matter of course, the tubing 5d is preferably made of a flexible and collapsible material for the purpose of enabling the effective cross sectional area thereof to be adjustable and also for the purpose of facilitating the connection of the tubing 5d with other piping elements, while it has an internal diameter relatively great enough to allow the blood flowing therethrough to be uniformly distributed into the dialyzer unit 3.

Referring back to FIG. 3, the dialyzer unit 3 has a dialysate chamber defined therein on one side of the semipermeable membrane opposite to the blood chamber and is connected through a dialysate inlet to a source of a dialyzing solution by means of a supplying passage on a one hand and through a dialysate outlet to a suitable dialysate reservoir (not shown) by means of an outflow passage 32. The supply passage leading from the source of the dialyzing solution to the dialysate inlet of the dialyzer unit 3 comprises a main passage 31 having an electromagnetic shut-off valve 33 located adjacent the connection of the main passage 31 to the dialysate inlet, a flow regulator 35 of any known construction and a flowmeter 36 of any known construction located substantially intermediately between the shut-off valve 35 and the flow regulator 35, and a bypass passage 38 bypassing both of the flow regulator 35 and the flowmeter 36 and having its opposite ends fluid-connected to respective portions of the main passage 31 upstream of the flow regulator 35 and upstream of the shutoff valve 33 with respect to the direction of flow of the dialyzing solution from the source thereof towards the dialysate inlet. The bypass passage 38 also has an electromagnetic shut-off valve 37 disposed therein. On the other hand, the outflow passage 32 has an electromagnetic shut-off valve 34 disposed therein and located adjacent the connection of the outflow passage 32 to the dialysate outlet. These electromagnetic shut-off valves 33, 34 and 37 are of any known construction and area of a design adapted to close and open the respective passage when electrically energized and deenergized, respectively. Preferably, these shut-off valves 33, 34 and 37 are made of chemical resistant material such as, for example, stainless steel. In addition, a bypass passage 38 is utilized when the dialyzing solution remaining within the dialysate chamber in the dialyzer unit 3 is desired to be replaced, and therefore, it is preferred to have as low a resistance to the flow as possible.

Hereinafter, the relationship between the nature of the signals generated from the pressure sensor 9 and the operation of each of the blood pump 2 and the electromagnetic shut-off valves 33, 34 and 37 will be described.

When and so long as the dialysis is performed adequately, the pressure sensor 9 generates no output signal; the blood pump 2 is operated at a predetermined number of revolution; the solenoid unit 22 is in a deenergized state while permitting the tubing 5d to be clamped or constricted to a predetermined effective cross sectional area; the electromagnetic shut-off valves 33 and 34 are opened; and the electromagnetic shut-off valve 37 is closed to disable the bypass passage 38. In this condition, the pumped blood flows through the blood chamber in the dialyzer unit 3 under a controlled positive pressure determined by the effective cross sectional area of the tubing 5d then clamped between the conical member 18b and the tailstock 28 of the positive pressure regulator 14, while the dialyzing solution is allowed to flow through the dialysate chamber in the same dialyzer unit 3 at a controlled rate.

However, when the pressure sensor 5 subsequently generates the first signal R in response to a reduction of the blood pressure to such an extent as to permit the pointer needle 11 to indicate a pressure reading equal to or lower than that indicated by the first index pointer 12, the solenoid unit 22 is energized to interrupt the application of the clamping force to the tubing 5d and, at the same time, the electromagnetic shut-off valves 33 and 34 are closed to interrupt the supply of the dialyzing solution through the dialysate chamber in the dialyzer unit 3. As a result of the tubing 5d is released from the clamping force, the ultrafiltration pressure decreases to about zero. In view of the interruption of the supply of the dialyzing solution through the dialysate chamber and the substantial absence of the ultrafiltration pressure, the removal of the excessive water component from the blood is interrupted to safeguard the patient. This condition continues even when the pointer needle 11 is once aligned with the first index needle 12 which further moves to a reading lower than the reading indicated by the first index needle 12 as a result of the further reduction of the pressure applied to the pressure sensor 9 through the sensing tube 5e. In addition, the pressure sensor 9 is so designed as to maintain the above described condition for a predetermined period of time, for example, about 10 minutes, even after the pressure applied to the sensor 9 is once reduced to a reading lower than the reading indicated by the first index needle 12 has increased to a reading with the first signal R consequently no longer generated from the sensor 9 to avoid any possible occurrence of chattering and also to safeguard the patient. The timing at which the counting of the predetermined period of time subsequent to the interruption of the generation of the signal R from the sensor 9 starts may be either at the time the sensor 9 has generated the first signal R or at the time the sensor 9 has ceased its generation of the first signal R.

It is to be noted that, during the interruption of the removal of the excessive water component from the blood effected in the manner described above, diffusion of substances from the blood in the blood chamber of the dialyzer unit 3 into the dialysate chamber takes place through the semipermeable membrane by the effect of the osmotic pressure. Accordngly, it is preferred to replenish the dialyzing solution within the dialysate chamber at appropriate intervals of time. For this purpose, arrangement is made to permit the electromagnetic shut-off valves 33, 34 and 37 to be opened for a predetermined short time at intervals of, for example, 1 minute. The shorter the time required for the solution within the dialysate chamber to be replenished, the better. The time required for the solution within the dialysate chamber to be replenished is determined by the amount of dialyzing solution primed into the dialysate chamber and the flow rate of the dialyzing solution during the replenishment and is generally 1 to a few seconds.

When during the interruption of the water removal the blood pressure increases to a value higher than the value at which the pressure sensor 9 no longer generates the first signal R, and after the predetermined period of time has passed subsequent to the interruption of the first signal R from the pressure sensor 9, the solenoid unit 22 is energized and the electromagnetic shut-off valves 33 and 34 are opened thereby to reinstate the water removal.

While the foregoing process takes place usually when the patient comes down with hypotonia as a result of the dialysis, it may also happen that the pressure of the blood flowing past the air trap 6a abruptly decreases for a physical reason. By way of example, this may happen when the opening at the tip of the cannula 1a is closed by contact with the wall of the blood vessel, or when a portion of the blood vessel around the pierced cannula 1a collapses to close the opening at the tip of the cannula 1a. Once this happens, it may bring about damage to the wall of the blood vessel unless immediate action is taken to immediately interrupt the blood pump 2. In any event, this abrupt decrease in pressure of the blood flowing past the air trap 6a is of a nature quite different from that resulting from, for example, hypotonia and, for detecting it, the second index needle 13 is utilized. More specifically, in view of the fact that the abrupt decrease in the pressure of the blood causes the pointer needle 11 to move down to a reading lower than the reading of pressure normally exhibited by the occurrence of hypotonia, that is, lower than the reading indicated by the first index needle 12, it can be detected when the pointer needle 11 moving down past the reading indicated by the first index needle 12 aligns with the second index needle 13. Thus, the second index needle 13 is provided for the purpose of detecting the occurrence of the abrupt decrease in pressure of the blood in cooperation with the pointer needle 1, and the pressure sensor 9 generates the second signal S when the pressure of the blood abruptly decreases to a value equal to or lower than the reading indicated by the second index needle 13. This second signal S is utilized not only to cause the electromagnetic shut-off valves 33 and 34 to be closed, but also to interrupt the blood pump 2. At the same time, the second signal S may be utilized to actuate an alarming device such as, for example, a buzzer and/or an indicator lamp, so that the attendant nurse having been notified of the occurrence of such an abnormal condition can readily and promptly take any necessary preventive measures to avoid a significant accident.

In practice, the dialyzing apparatus of the above described construction according to the present invention is utilized in the following manner. At the outset, the electromagnetic shut-off valves 33 and 34 are opened and the electromagnetic shut-off valve 37 is closed, to allow the flow rate of the dialyzing solution to be adjusted to a desired or required value in a manner known to those skilled in the art. Then, while the blood pump 2 is held at a standstill, the pressure under non-circulating time P1 is measured by the utilization of the pressure sensor 9. The pressure P1 under non-circulating time takes a positive value and is normally in the order of tens of mmHg. It is to be noted that the adjustment of the flow of the dialyzing solution and the measurement of the pressure under non-circulating time P1 may be carried out either simultaneously or at different occasions and, in the latter case, the flow adjustment may either follow or is followed by the pressure measurement.

Thereafter, the blood pump 2 is operated at a predetermined number of revolutions a required to allow the blood to be dialyzed to flow through the blood chamber in the dialyzer unit 3 at a proper flow rate. During the circulation of the blood through the extracorporeal blood circuit, the pressure during circulating time P2 is again measured by the use of the pressure sensor 9, which pressure during circulating time P2 prevailing during the blood circulation is of a value equal to the difference between the pressure during non-circulating time P1 prevailing during the interruption of the blood circulation and the amount of pressure dropped across the cannula 1a, and usually takes a negative value, i.e., a negative pressure. On the other hand, the first index needle 12 of the pressure sensor 9 is adjusted to a reading P3 which represents the difference between the shunt pressures P1 and P2, i.e., P3=P2−P1, while the second index needle 13 is adjusted to a reading P4 which is a value lower than the reading P3 by 50 to 100 mmHg, i.e., P4=P3−(50 to 100). Thus, it will readily be seen that the pressure difference P3 is lower than the pressure during circulating time P2 prevailing during the circulation of the blood by the pressure during non-circulating time P1 prevailing during the interruption of the blood circulation and that the pressure P4 to which the second index needle 13 has been adjusted is lower than the pressure P3 by 50 to 100 mmHg.

The effective cross sectional area of the tubing 5d is then adjusted by turning the known 27b and, hence, the adjustment screw 27 in either direction about its own longitudinal axis while the solenoid unit 22 is deenergized to allow the conical member 18b to be held in position close to the tailstock 28. As has been described previously, by adjusting the effective cross sectional area of the tubing 5d, a proper ultrafiltration pressure can be developed. This adjustment of the effective cross sectional area of the tubing 5d to establish the proper ultrafiltration pressure is carried out in the light of the reading given by the pressure gauge 7b as is well known to those skilled in the art. By way of example, where 2.4 lits. of water component is desired to be removed from the blood in 6 hours, the required ultrafiltration pressure will be 100 mmHg if the dialyzer unit 3 used is of a type having 4 ml/hr/mmHg is UFR (Ultrafiltration Rate). As a matter of practice, prior to the dialysis being performed, the blood pressure and other physical conditions of the patient are to be measured and examined.

With the dialyzing apparatus so adjusted in the way as hereinabove described, it is clear that, while the blood is circulated through the extracorporeal blood circuit by the action of the blood pump 2 at a controlled rate, the dialysis takes place under the controlled ultrafiltration pressure. As the water removal from the blood proceeds in this way, the amount of blood of the patient may decrease, it being, however, that the resultant reduction in blood pressure in the patient can be compensated for by the constriction of the blood vessels unless it is excessive. As the water removal from the blood further proceeds to such an extent as may result in a reduction of the blood pressure within the A-V fistula to which the cannula 1a has been pierced, the pressure within the tubing 5a correspondingly decreases and, if the pointer needle 11 of the pressure sensor 9 moves down to align with the first index needle 12 which has been set at the reading of pressure P3, the first signal R is generated from the pressure sensor 9. Consequent upon the generation of the first signal R from the pressure sensor 9, the solenoid unit 22 is energized to release the application of the clamping force from the tubing 5d with the result of the reduction of ultrafiltration pressure substantially to a zero value and, at the same time, the electromagnetic shut-off valves 33 and 34 are closed to interrupt the supply of the dialyzing solution through the dialysate chamber of the dialyzer unit 3, thereby interrupting the water removal from the patient's blood. During the interruption of the water removal that has taken place in this way, the electromagnetic shut-off valves 33, 34 and 37 are opened for several seconds at intervals of a predetermined time, for example, 1 minute, to allow the dialyzing solution to flow through the dialysate chamber in an increased amount so that the dialyzing solution within the dialysate chamber in the dialyzer unit 3 can be replenished over and over in a short period of time.

When the amount of blood in the patient eventually increases as the transfer of the body fluid into the A-V fistula progresses, and when the patient's blood pressure once reduced recovers, the pressure sensor 9 will no longer generate the first signal R. After the predetermined period of time subsequent to the interruption of the generation of the first signal R, the solenoid unit 22 is deenergized, the electromagnetic shut-off valves 33 and 34 are opened and the electromagnetic shut-off valve 37 is closed, thereby reinstating the normal dialyzing operation.

In this way, without the patient's sympton of hypotonia from the dialysis being substantially aggravated, the blood dialysis can be performed normally throughout the time required. In the event that the pressure inside the tubing 5a abruptly drops by some physical reason, this pressure deop is in turn introduced into the pressure sensor 9 through the tubing 5d and the pointer needle 11 is consequently moved downwards, as viewed in FIG. 2, to a reading equal to or lower than the reading indicated by the second index needle 13. Upon the alignment of the pointer needle 11 with the second index needle 13, the pressure sensor 9 generates the second signal S with which the blood pump 2 is interrupted, in addition to the energization of the solenoid unit 22 and the closure of the elctromagnetic shut-off valves 33 and 34. At the same time, the second indicator lamp 13a is lit and the alarming device may be actuated, thereby to notify the attendant nurse of the occurrance of the abornmal condition.

With the dialzing apparatus according to the present invention described with reference to and shown in FIGS. 3 to 6, the blood dialysis can be performed with no substantial need to measure the patient's blood pressure so frequently and also to adjust the ultrafiltration pressure depending on the measured blood pressure. More specifically, in view of the fact that the concentration of the patient's blood increases with the progress of the water removal from the blood, accompanied by the increased flow resistance inside the cannula 1a with the consequent increase of the pressure drop, the pressure inside the tubing 5a correspondingly decreases. However, since the pressure sensor 9 generates the first signal R prior to the blood pressure being decreased to a critical value, any further undesirable decrease of the blood pressure can be advantageously avoided, thereby safeguarding the patient.

Where depending on the patient an increase of the blood concentration cannot be expected, and/or where by some reason a latitude is desired to be allowed for the purpose of increased safety, the first index needle 11 has to be set at a reading equal to 90 to 95% of the pressure difference P3 discussed hereinbefore. In addition, although in the foregoing description the pressure difference P3 has been described as determined by the utilization of the measured pressures P2 and P1 prevailing respectively during the blood circulation and the interruption of the blood circulation in such a way as to yield the difference therebetween, a simplified method for the determination of the pressure difference P3 is possible by the use of and making reference to a table or graph in which the amount of pressure drop as a function of parameters such as hematocrit and blood flow rate is described for each of the cannulus of different internal diamters. A series of experiments conducted by the inventors of the present invention using the above described two methods have shown that the pressure difference P3 determined by the use of the measured shunt pressures P2 and P1 matches substantially with that determined by the simplified method.

The pressure sensor 9 has been described as of such a design that the first and second signals R and S can be generated upon the alignment of the movable pointer needle 11 with the manually presettable index needles 12 and 13, respectively, one at a time. However, the pressure sensor 9 utilizeable in the practice of the present invention may not be always limited to such a design, but may be of a type comprising a pressure gauge or semiconductor pressure sensor capable of converting the detected pressure into an electric signal, and comparators capable of comparing the pressure signal so converted with a predetermined voltage for generatng the respective first or second signal. In such case, a sensor element, that is, either the pressure gauge or the semiconductor sensor, of the pressure sensor 9 can be mounted direct on the tubing 5a, the cannula 1a or the blood pump 2.

The pressure gauge 7b used in the embodiment of the present invention described hereinabove is of a type having an adjustable needle presettable to a reading of the uppermost permissible pressure and capable of generating, when the pressure detected thereby increases to a value equal to or higher than the uppermost permissible value, a signal utilizeable to interrupt the blood pump 2 and also to issue an audible and/or visual signal.

Moreover, although reference has been made to a positive pressure regulator 14 used as means for generating a ultrafiltration pressure in the flow of the blood through the blood chamber in the dialyzer unit 3, it may be employed in combination with an orifice hitherto used in the prior art apparatus. In such case, the positive pressure regulator 14 shuld be fluid-connected in parallel to the orifice and may not be always required to have the capability of adjusting the effective cross sectional area of the tubing 5d.

Where a heater device for heating the dialyzing solution is incorporated in the apparatus according to the present invention, arrangement should be made in such a way that the heater device can be electrically deenergized simultaneously with the interruption of the supply of the dialyzing solution through the dialysate chamber of the dialyzer unit 3, or that although the heater device need not be electrically deenegized, the dialyzing solution flowing towards the dialysate chamber can bypass the dialysate chamber for the purpose of avoiding any possible overheating of the dialyzing solution within the dialysate chamber.

The concept of the present invention hereinbefore described as applied in the system utilizing a positive ultrafiltration pressure can equally be applicable to a system ulitizing a negative ultrafiltration pressure. This will now be described with particular reference to FIG. 7.

Figure 7:
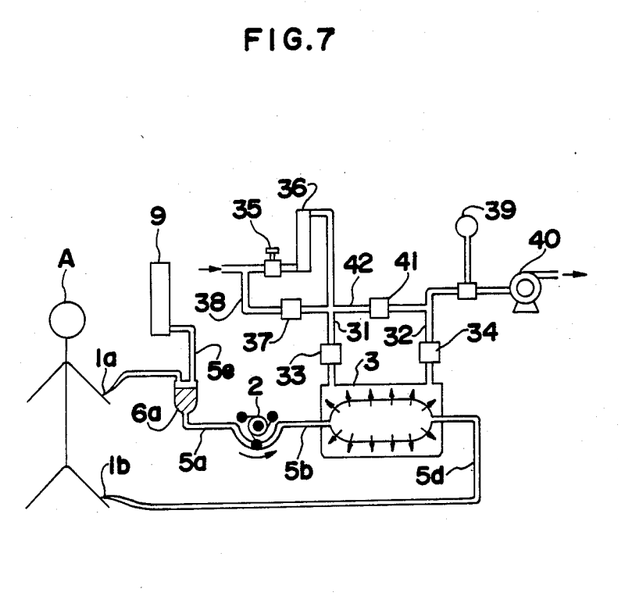
FIG. 7 is a diagram similar to FIG. 3, showing another preferred embodiment of the present invention.

In the system utilizing the negative ultrafiltration system shown in FIG. 7, the tubing 5d which has been described as having the air trap 6b, the pressure gauge 7b and the positive pressure regulator 14 in the foregoing embodiment shown in FIGS. 3 to 6 is fluid-connected direct to the blood outlet cannula 1b from the blood outlet of the blood chamber in the dialyzer unit 3. A portion of the outflow passage 32 between the electromagnetic shut-off valve 34 and a discharge pump 21 is fluid-connected to a pressure, and the junction between a downstream end of the bypass passage 38 and the main passage 31 is fluid-connected by means of a second bypass passage 42, having an electromagnetic shut-off valve 41 disposed therein, to a portion of the outflow passage 32 downstream of the shut-off valve 34 and upstream of the pressure sensor 39. During the dialyzing operation being performed, the discharge pump 40 is constantly operated and the pressure on the suction side of the discharge pump 40 is measured and monitored by the pressure sensor 39. The electromagnetic shut-off valve 41 is operatively associated with the pressure sensor 9, as is the case with the electromagnetic shut-off valves 33, 34 and 37, so that during the dialysis taking place with the water removal being performed, it can be closed, but is opened when the electromagnetic shut-off valves 33 and 34 are closed in response to the first signal R thereby bypassing the dialyzing solution without being supplied to the dialysate chamber in the dialyzer unit 3. In the case of the replenishment of the dialyzing solution within the dialysate chamber and when the electromagnetic shut-off valve 33, 34 and 37 are therefore opened, this electromagnetic shut-off valve 41 is closed.

Where the dialyzing apparatus according to the embodiment shown in FIG. 7 is to be used in practice, the pressure sensor 9 has to be adjusted in the manner as hereinbefore described in connection with the foregoing embodiment on the one hand and, on the other hand, the number of revolutions of the discharge pump 40 and the flow regulator 35 have to be adjusted so that the dialyzing solution can be supplied at a required flow rate and can flow through the dialysate chamber under a pressure required to establish a proper ultrafiltration pressure inside the dialyzer unit 3. While the dialysis is performed with the use of the apparatus according to the embodiment shown in FIG. 7, and when the first signal R is generated from the pressure sensor 9, the electromagnetic shut-off valves 33 and 34 are closed and the electromagnetic shut-off valve 41 is opened and, accordingly, the dialyzing solution flows through the second bypass passage 42 and then to the reservoir through the pump 40 without being supplied into the dialysate chamber. Accordingly, the ultrafiltration pressure is consequently reduced to about zero and the water removal from the blood is interrupted. Where the dialysate chamber is replenished with the dialyzing solution, the electromagnetic shut-off valves 33, 34 and 37 are opened while the electromagnetic shut-off valve 41 is closed and, accordingly, the replenishment is completed in a short period of time.

In the second embodiment described with reference to and shown in FIG. 7, the ultrafiltration pressure generating means is constituted by the flow regulator 35 disposed on the main passage 31 and the discharge pump 40 disposed on the outflow passage 32. Therefore, it has been described that, in order to reduce the ultrafiltration pressure to about zero, the electromagnetic shut-off valves 33 and 34 and the electromagnetic shut-off valve 41 are adapted to be closed and opened, respectively. However, as an alternative method of reducing the ultrafiltration pressure to about zero, arrangement may be made to interrupt the discharge pump 40, and in such case, the second bypass passage 42 with the electromagnetic shut-off valve 41 may be omitted and the electromagnetic shut-off valve 34 may also be omitted provided that the discharge pump 40 is of a type which, when brought to a halt, will not allow the dialyzing solution to flow therethrough. Moreover, a discharge passage with an electromagnetic shut-off valve for the purpose of the replenishment of the dialyzing solution may be separately provided upstream of the discharge pump 40. In addition, the downstream end of the bypass passage 38, which has been described and shown as connected to the portion of the main passage 31 upstream of the shut-off valve 33, may be connected to a portion of the main passage 31 downstream of the shut-off valve 33.

In any one of the first and second preferred embodiments of the present invention shown respectively in FIGS. 3 to 6 and FIG. 7, the frequent necessity of blood pressure measurement and the incident adjustment of the rate of the water removal can advantageously be minimized. Also, it is possible to avoid any possible excessive reduction in blood pressure resulting from the excessive removal of the water component from the blood on the one hand and the water removal rate can advantageously be maximized with a consequent high clearance and efficiency on the other hand, In the event of the occurrence of an abnormal condition such as a trouble with the cannula 1a, the pump is immediately brought to a halt for safeguarding the patient, and therefore, the necessity for the patient to be watched from time to time can advantageously be minimized while the shunt is protected. In addition, since even during the interruption of the water removal, the dialyzing solution within the dialysate chamber is replenished at intervals of the predetermined time, diffusion of substances from the blood into the dialysate chamber continues by the effect of the osmotic pressure. Moreover, since the replenishment of the dialyzing solution is completed in a short time as hereinbefore descirbed, the water removal from the blood does not take place substantially. As a matter of course, the apparatus according to the present invention can function satisfactorily and effectively even when the amount of water to be removed from the blood is relatively small, and even in that case, both the dialysis and the water removal take place in a stabilized manner.

Thus, according to the present invention, it is clear that the necessity of frequent blood pressure measurements of the patient and the incident adjustment of the water removal rate can be minimized and that the patient can be protected from any possible hypotonia resulting from the excessive water removal while the dialysis can be performed in a stabilized manner with high efficiency. It is also clear that, een during the interruption of the water removal, substances contained in the blood other then the water component can diffuse into the dialyzing solution by the effect of the osmotic pressure, and therefore the clearance of the apparatus can be increased.

In view of the foregoing, it is possible to reduce the time required to the patient to be bound to the dialyzing apparatus and also to minimize the occurrence of accidents. Therefore, the apparatus according to the present invention is advantageous in that the safety factor is high while contributing to a reduction in the cost required to perform the dialyzing operation to the patient.

Although the present invention has fully been described in connection with the preferred embodiments thereof with reference to the accompanying drawings, it is to be noted that various changes and modifications are apparent to those skilled in the art. By way of example, in any one of the first and second embodiments, although it has been described that the first signal R is utilized to adjust the ultrafiltration pressure to about zero, it is possible to adjust the ultrafiltration pressure in dependence on the change in pressure inside the tubing 5a that is detected by the pressure sensor 9. Moreover, a computer-controlled scheme is also possible to perform a safe and efficient dialyzing operation based on the data of physical conditions of the patient, the data of operational parameters of the equipments of the apparatus, and a program necessary to obtain a proper ultrafiltrationpressure on the basis of the pressure inside the tubing 5a and various data. In such case, servomotors and servo valves may be employed.

Accordingly, such changes and modifications are to be understood as included within the scope of the present invention as defined by the appended claims, unless they depart therefrom.

What is claimed is:

1. A method of dialyzing the blood by use of a dialyzer having a semipermeable membrane dividing the interior of the dialyzer into a blood chamber and dialysate chamber, which method comprises the steps of:
   measuring the pressure of the blood during the interruption of blood circulation by the use of a pressure sensor disposed on the upstream side of a blood pump while the operation of said blood pump is stopped;
   measuring the pressure of the blood during blood circulation by the use of said pressure sensor while the blood pump is in operation;
   obtaining a value by subtracting the measured value of the pressure during interruption of the blood circulation which in turn is multiplied by a coefficient less than one from the measured value of the blood pressure during the circulation of the blood;
   setting said value as a predetermined value at a setting means;
   reducing a ultrafiltration pressure to substantially zero from the normal pressure, if said pressure sensor detects a value of pressure that is equal to or less than the predetermined value while the blood pump is in operation; and
   bringing the ultrafiltration pressure back to normal pressure when said pressure sensor no longer detects a value of pressure that is equal to or below the predetermined value.

2. An apparatus for dialyzing the blood by the use of a dialyzer having a semipermeable membrane functioning to divide the interior of the dialyzer into a blood chamber and a dialysate chamber, which apparatus comprises;
   a blood pump for feeding the blood into the blood chamber;
   a pressure sensor for detecting the pressure of the blood, that is provided at a midway point of a tubing disposed on the upstream side of the said blood pump;
   a means for obtaining a value by subtracting a value of the pressure during interruption of the blood circulation which is multiplied by a coefficient less than one from a value of the blood pressure that is detected by the use of said pressure sensor in the initial stage of dialysis while the blood is in circulation;
   a setting means for setting said value as a predetermined value; and
   a control means for reducing an ultrafiltration pressure in the dialyzer to substantially zero without halting the operation of the blood pump if the pressure sensor detects a pressure with a value that is equal to or less than the predetermined value.

3. An apparatus as claimed in claim 2, further comprising means for generating the ultrafiltration pressure in the dialyzer, and first and second shut-off valves disposed in a supply passage for the supply of a dialzing solution from a source thereof towards the dialysate chamber and a discharge passage for the discharge of the dialyzing solution, which has passed through the dialysate chamber, from the dialysate chamber to the outside, respectively, said first and second shut-off valves being adapted to be closed in the event that the pressure of the blood so detected attains the value equal to or lower than the predetermined value.

4. An apparatus as claimed in claim 3, wherein said ultrafiltration pressure generating means comprises a positive pressure regulator for adjustably clamping a tubing, fluid-coupled to a blood outlet of the blood chamber, to control the effective cross sectional area thereof.

5. An apparatus as claimed in claim 4, wherein said positive pressure regulator comprises a presser element supported for movement between retracted and clamping postions, a stationary block for the support of the tubing when the tubing is clamped to reduce the effective cross sectional area thereof by the presser element then moved from the retracted position to the clamping position, and means for adjusting the position of the stationary block relative to the presser element.

6. An apparatus as claimed in claim 5, wherein said adjusting means comprises an adjustment screw having one end operatively coupled with the stationary block.

7. An apparatus as claimed in claim 3, wherein said ultrafiltration pressure generating means comprises a throttling means disposed on the supply passage and a discharge pump disposed on the discharge passage at a location downstream of the second shut-off valve with respect to the direction of flow towards the outside.

8. An apparatus as claimed in claim 3, wherein said first and second shut-off valves are opened for a predetermined short time at intervals of a predetermined time during the closure thereof as a result of the pressure of the blood having attained the value equal to or lower than the predetermined value.

* * * * *